(12) United States Patent
Kekonen et al.

(10) Patent No.: US 11,890,106 B2
(45) Date of Patent: Feb. 6, 2024

(54) MEASURING WOUND HEALING

(71) Applicant: CutoSense Oy, Turku (FI)

(72) Inventors: Atte Kekonen, Tampere (FI); Mikael Bergelin, Turku (FI); Jan-Erik Eriksson, Turku (FI); Max Johansson, Turku (FI)

(73) Assignee: CutoSense Oy, Turku (FI)

( * ) Notice: Subject to any disclaimer, the term of this patent is extended or adjusted under 35 U.S.C. 154(b) by 775 days.

(21) Appl. No.: 16/618,130

(22) PCT Filed: May 31, 2018

(86) PCT No.: PCT/EP2018/064353
§ 371 (c)(1),
(2) Date: Nov. 28, 2019

(87) PCT Pub. No.: WO2018/220121
PCT Pub. Date: Dec. 6, 2018

(65) Prior Publication Data
US 2020/0170565 A1    Jun. 4, 2020

(30) Foreign Application Priority Data
May 31, 2017    (EP) .................................. 17173840

(51) Int. Cl.
*A61B 5/00* (2006.01)
*A61B 5/0531* (2021.01)

(52) U.S. Cl.
CPC ............ *A61B 5/445* (2013.01); *A61B 5/0531* (2013.01); *A61B 5/68* (2013.01)

(58) Field of Classification Search
CPC ......... A61B 5/445; A61B 5/0531; A61B 5/68; A61B 2562/046
See application file for complete search history.

(56) References Cited

U.S. PATENT DOCUMENTS

| | | | |
|---|---|---|---|
| 2011/0313311 A1* | 12/2011 | Gaw .................... | A61B 5/4331 600/547 |
| 2016/0081580 A1* | 3/2016 | Bergelin ............... | A61B 5/445 600/554 |

(Continued)

FOREIGN PATENT DOCUMENTS

| CN | 106377256 A | 2/2017 |
|---|---|---|
| JP | 2006508732 A | 3/2006 |
| WO | WO2015195720 A1 | 12/2015 |

OTHER PUBLICATIONS

Weber et al: Remote wound monitoring of chronic ulcers. IEEE Transactions on Information Technology in Biomedicine, Mar. 2010, vol. 14, No. 2, pp. 371-377.

(Continued)

*Primary Examiner* — Mallika D Fairchild
*Assistant Examiner* — Shreya Anjaria
(74) *Attorney, Agent, or Firm* — Laine IP Oy

(57) ABSTRACT

According to an example aspect of the present invention, there is provided method for measuring wound healing, comprising, measuring a wound impedance by a first tetrapolar arrangement of electrodes arranged on both sides of a wound, measuring a reference impedance by a second tetrapolar arrangement of electrodes arranged on one side of the wound, determining, by a controller, wound healing on the basis of the wound impedance and the reference impedance measured over a frequency range.

15 Claims, 3 Drawing Sheets

(56) References Cited

U.S. PATENT DOCUMENTS

2016/0101282 A1   4/2016   Bergelin et al.
2016/0150994 A1   6/2016   Smith

OTHER PUBLICATIONS

Kekonen et al: Bioimpedance measurement based evaluation of wound healing. Physiol Meas, 2017.
Kekonen et al: A Quantitative Method for Monitoring Wound Healing. International Journal of Bioelectromagnetism, 2015, vol. 17, No. 1, pp. 36-41.
Lukaski et al: Bioelectrical Impedance Assessment of Wound Healing. Journal of Diabetes Science and Technology, Jan. 2012, vol. 6, Issue 1, pp. 209-212.

* cited by examiner

MEASURING WOUND HEALING

FIELD

The present invention relates to methods of evaluating wound healing. In particular, the present invention concerns a method of measuring wound healing which is suitable, for example, in evaluation of wound healing in situations where the wound is closed and the wound bed is not exposed. The present invention also concerns an arrangement for carrying out such a method.

BACKGROUND

Acute surgical wounds are often closed using sutures. In certain cases, keeping the affected part of the body stationary is required. Evaluation of the timely healing of wounds, which are covered long-term by an orthopaedic cast or similar, is difficult with the conventional visual means.

Bioimpedance describes the passive electrical properties of biological materials. Bioimpedance measurements are used in various applications in example for diagnostic and monitoring purposes. Bioimpedance measurements provide a safe, non-invasive and objective way to assess cellular level architecture and function. The applications include pneumography, tissue characterization, impedance tomography, skin cancer detection and lymphedema monitoring.

Known configurations for measuring bioimpedance comprise a monopolar (three-electrode configuration), bipolar and tetrapolar configurations. The monopolar and the bipolar configurations measure the impedance of the tissue directly under the electrode, in addition to the impedance of the deeper tissue layers. Both setups are affected by the electrode impedance. Sensitivity of the monopolar and the bipolar measurement is highest under the electrode and decreases with distance from the electrode. The monopolar measurement is also affected by negative areas of sensitivity.

Kekonen A, Bergelin M, Eriksson J-E, Vaalasti A, Ylänen H, Viik J (2017) Bioimpedance measurement based evaluation of wound healing. Physiol Meas DOI:10.1088/1361-6579/aa63d6, discloses applying a bipolar method for the evaluation of wound healing.

However, neither the bipolar nor the monopolar method can be used for evaluation of wound healing when the wound is closed and the wound bed is not exposed.

Tetrapolar method has been used for assessing the fluid status of human body and it has also been used for monitoring the effectiveness of lymphedema treatment.

SUMMARY OF THE INVENTION

The invention is defined by the features of the independent claims. Some specific embodiments are defined in the dependent claims.

According to a first aspect of the present invention, there is provided a method for measuring wound healing, comprising, measuring wound impedance by a first tetrapolar arrangement of electrodes arranged on both sides of a wound, measuring reference impedance by a second tetrapolar arrangement of electrodes arranged on one side of the wound, determining, by a controller, wound healing on the basis of the wound impedance and the reference impedance measured over a frequency range.

According to a second aspect of the present invention, there is provided an arrangement for measuring wound healing comprising, a first tetrapolar arrangement of electrodes arranged on both sides of a wound for measuring wound impedance, a second tetrapolar arrangement of electrodes arranged on one side of the wound for measuring reference impedance, and a controller caused to determine wound healing on the basis of the wound impedance and the reference impedance measured over a frequency range.

EMBODIMENTS

Figure 1A:
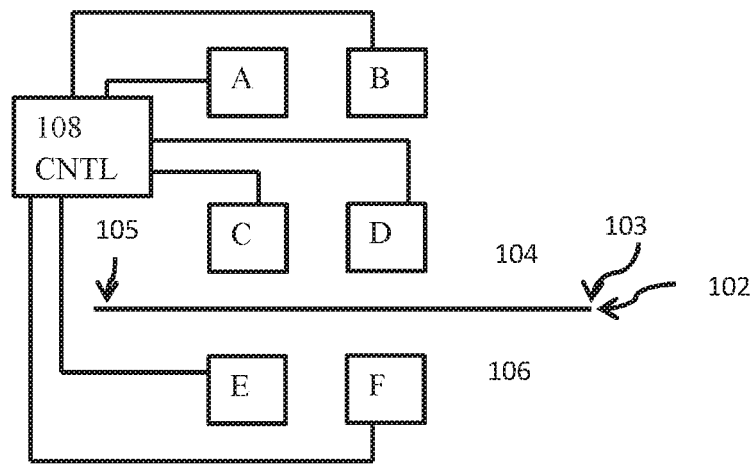
FIG. 1A and FIG. 1B illustrate arrangements for measuring wound healing in accordance with at least some embodiments.
Figure 1B:
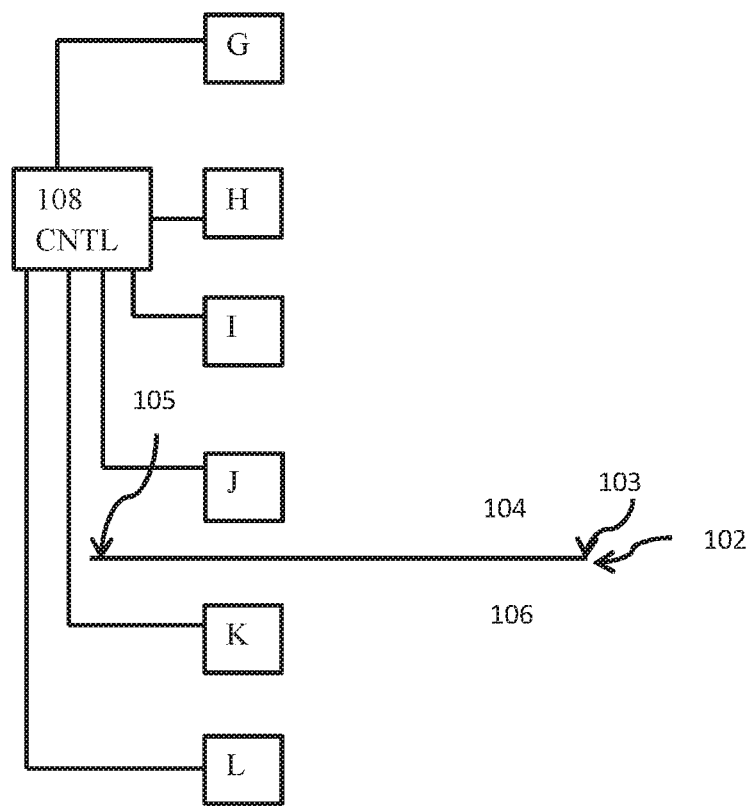

FIG. 1A, and FIG. 1B illustrate arrangements for measuring a wound healing in accordance at least some embodiments. The arrangements comprise a first tetrapolar arrangement of electrodes arranged on both sides 104, 106 of a wound 102 for measuring a wound impedance and a second tetrapolar arrangement of electrodes arranged on one side of the wound for measuring a reference impedance. The arrangements may be caused to determine wound healing on the basis of the wound impedance and the reference impedance measured over a frequency range. The tetrapolar arrangements of electrodes provide that influences originating from the superficial layers of the tissue and from the electrodes may be eliminated for determining wound healing.

In an embodiment, the wound impedance and reference impedance are measured in a time-division manner by at least partly shared electrodes. In this way interference between the wound impedance measurement and reference impedance measurement may be avoided as well as fewer electrodes are needed.

A tetrapolar arrangement of electrodes comprises four electrodes. Two tetrapolar arrangements of electrodes may be provided by eight or a lower number of electrodes that are at least in part shared by the tetrapolar arrangements. Sharing of the electrodes may be achieved such that the tetrapolar arrangements use one or more shared electrodes at separate times, whereby the measurements using the tetrapolar arrangements may be performed in a time-division manner.

In an embodiment, an arrangement according to an embodiment comprises a controller 108 connected to the electrodes. The controller may be configured to cause determining wound healing on the basis of the wound impedance and the reference impedance measured over a frequency range. The controller may be a computer, a processor, a memory device, a computer program and/or a virtual machine. In an example, the controller may be implemented by a computer program stored on a memory device accessible to a computer, a processor and/or a virtual machine for execution of the code for determining wound healing on the basis of the wound impedance and the reference impedance measured over a frequency range. Connections between the controller and electrodes may comprise electrical conductors for example.

The tetrapolar arrangements may follow a measurement principle, where electrodes of the tetrapolar arrangement are connected to a target tissue, e.g. to skin of the subject, for measuring a wound impedance and a reference impedance. The tetrapolar arrangements comprise a first pair of electrodes that apply an excitation signal that causes a current flow in the target tissue. The tetrapolar arrangement further comprises a second pair of electrodes for measuring an impedance based on a voltage difference induced from the excitation signal applied to the tissue. The excitation signal may have a known magnitude and frequency, whereby the impedance may be then calculated using the extended Ohm's law.

Accordingly, a tetrapolar arrangement is fundamentally a two-port system with four terminals (electrodes). One port with two current feeding electrodes and one port with two voltage sensing electrodes. Because there are two ports in the system the tetrapolar arrangement measures the transfer function between these two ports which is called the transfer impedance. Therefore if the measured impedance is for example 0 ohms this does not imply the electrical conductivity is extremely high, but that there is no signal transfer between the two ports. It is important to understand that the tetrapolar arrangement does not measure the absolute electrical impedance (true impedance).

The tetrapolar arrangement of electrodes arranged on one side of the wound 102 for measuring a reference impedance provides that the effect of the wound to the reference impedance measurement may be avoided or at least decreased such that an impedance value indicating a healthy tissue may be obtained.

The tetrapolar arrangement of electrodes arranged on both sides of a wound 102 provides that the wound may be included in an electrical circuit formed by the electrodes feeding the excitation signal and the electrodes used to measure the voltage difference. In this way the wound impedance may provide information for determining wound healing.

The wound 102 has typically an elongated form between two ends 103, 105 of the wound. Tissue around the wound may be considered healthy tissue. The ends of the wound may be defined at locations, where the distance between across the wound is the largest. A line between the ends 103, 105 may separate different sides of the wound for purposes of measurements by the tetrapolar arrangements.

The wound 102 may be caused by surgery or injury to a biological material capable of being reconstructed, e.g. healed, by a biological process. The wound may be an internal to the biological material. An internal wound may be under the skin. Examples of internal wounds comprise encapsulated wounds or internal traumas. Examples of the biological material comprise living tissue for example human tissue or animal tissue. The tissue may be skin and/or fascia under the skin. In an example a surgical wound is typically closed after surgery by sutures. The surgical wound may be deep and even if the skin is healed the deep fascia may be still in the process of healing.

Measurements of wound impedance and reference impedance by tetrapolar arrangements using least in part shared electrodes are described next with reference to FIG. 1A and FIG. 1B. Accordingly, electrodes used for measuring the wound impedance and the reference impedance may be at least partly the same since used in a time division manner by the tetrapolar arrangement for measuring wound impedance and by the tetrapolar arrangement for measuring reference impedance.

In FIG. 1A, the arrangement comprises electrodes E and F on one side 106 of the wound 102 and electrodes A, B, D and D on another side 104 of the wound. A wound impedance may be measured by a tetrapolar arrangement comprising the electrodes C, D, E and F that are arranged on both sides of the wound 102. In one example, a wound impedance may be measured by a tetrapolar arrangement of electrodes C, D, E and F such that an excitation signal may be fed by the electrodes C and E and a voltage difference induced by the excitation signal may be measured by the electrodes D and F. In another example a wound impedance may be measured by a tetrapolar arrangement of electrodes C, D, E and F such that an excitation signal may be fed by the electrodes C and D and a voltage difference induced by the excitation signal may be measured by the electrodes E and F. In another example, a wound impedance may be measured by a tetrapolar arrangement of electrodes C, D, E and F such that an excitation signal may be fed by the electrodes C and F and a voltage difference induced by the excitation signal may be measured by the electrodes E and D.

Referring to FIG. 1A, a reference impedance may be measured by a tetrapolar arrangement comprising the electrodes A, B, C and D on one side of the wound. In one example, the reference impedance may be measured by a tetrapolar arrangement of electrodes A, C, B and D such that an excitation signal may be fed by the electrodes A and C and a voltage difference induced by the excitation signal may be measured by the electrodes B and D.

In another example a reference impedance may be measured by a tetrapolar arrangement of electrodes A, C, B and D such that an excitation signal may be fed by the electrodes A and D and a voltage difference induced by the excitation signal may be measured by the electrodes C and B. In another example, a wound impedance may be measured by a tetrapolar arrangement of electrodes A, B, C and D such that an excitation signal may be fed by the electrodes A and B and a voltage difference induced by the excitation signal may be measured by the electrodes C and D.

In FIG. 1B, the arrangement comprises electrodes K and L on one side 106 of the wound 102 and electrodes A, B, D and D on another side 104 of the wound. A wound impedance may be measured by a tetrapolar arrangement comprising the electrodes I, L, J and K that are arranged on both sides of the wound 102. In one example, a wound impedance may be measured by a tetrapolar arrangement of electrodes I, L, J and K such that an excitation signal may be fed by the electrodes I and L and a voltage difference induced by the excitation signal may be measured by the electrodes J and K.

Referring to FIG. 1B, a reference impedance may be measured by a tetrapolar arrangement comprising the electrodes G, H, I and J on one side 104 of the wound. In one example, the reference impedance may be measured by a tetrapolar arrangement of electrodes G, H, I and J such that an excitation signal may be fed by the electrodes G and J and a voltage difference induced by the excitation signal may be measured by the electrodes H and I.

It should be appreciated that the value of the transfer impedance is dictated by the sensitivity distribution of the measurement. The sensitivity distribution determines how much and in what way each region of the tissue contributes to the impedance signal. The sensitivity can be either positive, negative or neutral. An increase in resistivity in the area of positive sensitivity increases the measured impedance. In the area of negative sensitivity, the effect is opposite. The electrode placement affects the sensitivity distribution and therefore, it is desirable to obtain as high as possible positive sensitivity in the area of interest and as small as possible area of negative sensitivity.

Figure 2:
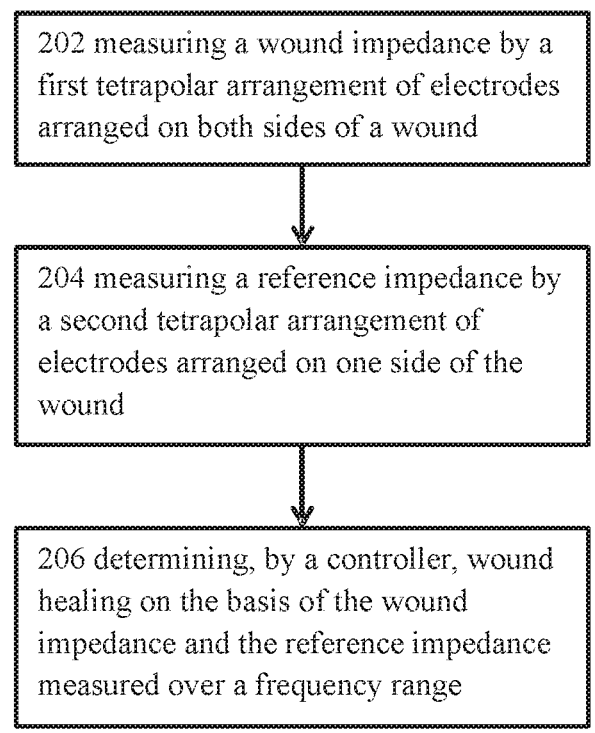
FIG. 2 illustrates a method in accordance with at least some embodiments.

FIG. 2 illustrates a method in accordance with at least some embodiments. The method may be performed by the arrangement described with FIG. 1A or 1B. Phase 202 comprises measuring a wound impedance by a first tetrapolar arrangement of electrodes arranged on both sides of a wound. Phase 204 comprises measuring a reference impedance by a second tetrapolar arrangement of electrodes arranged on one side of the wound Phase 206 comprises determining, by a controller, wound healing on the basis of the wound impedance and the reference impedance measured over a frequency range.

The measurements by the tetrapolar arrangements in phases 202 and 204 may use an excitation signal having a suitable magnitude and frequency for determining wound healing. In an example the excitation signal is a sinusoidal excitation signal having a magnitude 0.4 $V_{RMS}$ and a frequency between 150 Hz to 40 kHz. It should be appreciated that the magnitude and frequency may be varied depending on the wound that is being measured. Also, frequencies lower than 150 Hz may yield measurement results indicating an amount of extra cellular fluid and the electric current cannot pass the capacitive cellular membranes. On the other hand frequencies higher than 40 kHz may yield measurement results, where the measured impedance reflects the volume of extracellular fluid and intracellular fluid combined, as the reactance of the cellular membranes diminishes with the increasing frequency. At such high frequencies the impedance value or correspondence between the wound impedance and the reference impedance may erroneously indicate that the wound has healed.

In an embodiment, the frequency range comprises frequencies, where an excitation signal of the first and/or or second tetrapolar arrangements cause conduction of the current along cellular membrane surfaces. It should be appreciated that the frequency range is preferably such, where tetrapolar arrangement used for measuring the wound impedance cause conduction of the current along cellular membrane surfaces such that healing of the wound may be determined. Accordingly, the excitation signal provides that conductivity along the cellular membrane in the tissue is sufficiently high to distinguish changes in cell-cell contacts from the measured impedance response. The conductivity is sufficient at least when the surfaces of the cells, or the electrolyte volume at the surface of the cells, will begin to conduct better than the bulk extracellular fluid and the current will travel via the cellular membranes and through the extracellular fluid between the cells. In an example, conduction of the current along the cellular membrane surface may be provided using a high enough frequency for the ions to enrich on the surfaces of the cellular membrane. It should be appreciated that the cellular membrane surfaces may be of adipose tissue cells, connective tissue cells, muscle tissue cells and epithelial cells.

It should be appreciated that the excitation signal may have frequencies that allow observing an improved current conduction along cellular membrane surfaces as the healing of the wound progresses. Indeed, the wound impedance is significantly affected by the capability of the cellular membranes to conduct electricity. The capability of the cellular membranes to conduct electricity is negatively affected by missing and/or damaged cellular membranes in the wound, whereby at the beginning of the healing, the wound impedance is high. When the healing of the wound progresses, cells are generated and cellular membranes are reconstructed, whereby the capability of the wound to conduct electricity is improved and the wound impedance is decreased.

On the other hand, it should be appreciated that frequencies at the high end of the frequency range should be sufficiently low to hinder the current from passing through the cellular membrane.

Figure 3:
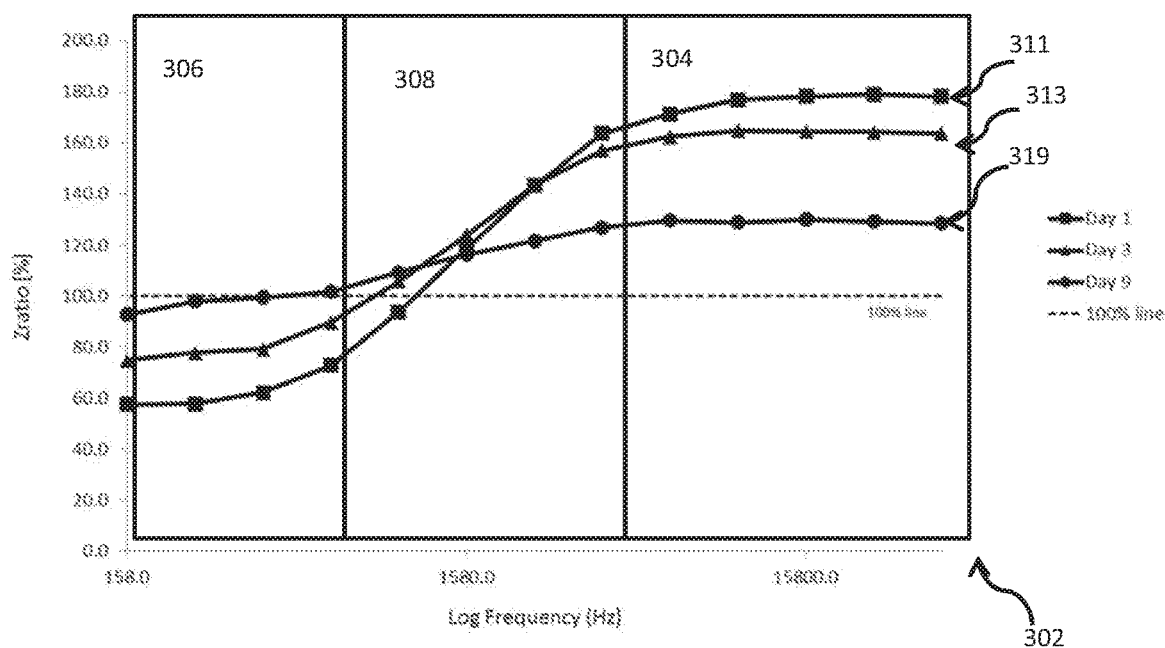
FIG. 3 illustrates a frequency response of wound healing measured in accordance with at least some embodiments.

FIG. 3 illustrates wound healing measured in accordance with at least some embodiments. The wound healing is illustrated by a frequency response 302 obtained by measuring wound impedance and reference impedance for example according to the method of FIG. 2. The frequency response illustrated in FIG. 3 was obtained by using a sinusoidal excitation signal having a magnitude 0.4 $V_{RMS}$ and a frequency between 150 Hz and 40 kHz. However, it should be appreciated that various embodiments described herein may be performed using excitation signals having different magnitudes and/or frequencies. The frequency response illustrates correspondence between the wound impedance and the reference impedance on a logarithmic frequency scale on a first post-operative day 311, third post-operative day 313 and on the ninth post-operative day 319. In FIG. 3 the frequency response is illustrated on a logarithmic scale.

In an embodiment, at least one level of the wound healing may be determined on the basis of at least one of a) a correspondence between the wound impedance and the reference impedance, and b) a change of the correspondence over at least part of the frequency range.

The correspondence between the wound impedance and the reference impedance may be a ratio of the wound impedance and the reference impedance, according to formula 1:

$$Z(f_n)_{ratio}[\%] = \left\{ \frac{Z(f_n)_W}{Z(f_n)_H} \right\} * 100\% \qquad (1)$$

where $Z(f_n)_w$ is the absolute value of wound impedance at the frequency n, $Z(f_n)_H$ is the absolute value of reference impedance at the frequency n and the $Z(f_n)$ratio is the ratio of the $Z(f_n)W$ and $Z(fn)H$ in percentages at the frequency n. The change of the correspondence over at least part of the frequency range may be obtained as a derivative of the $Z(f_n)_{ratio}$. A value of the change at a specific frequency may be obtained on the basis of the slope of the $Z(f_n)_{ratio}$ at the specific frequency for determining a level of the wound healing.

It should be noted that the frequency response in FIG. 3 may be referred to as frequency ratio response, when the correspondence between the wound impedance and the reference impedance is a ratio of the wound impedance and the reference impedance.

One or more thresholds for $Z(f_n)_{ratio}$ may be determined for the whole frequency range or at least part of the frequency range for determining wound healing. When the $Z(f_n)_{ratio}$ meets a determined threshold, a level of wound healing corresponding to the threshold may be determined. A level of wound healing may comprise "healed" and "not healed", for example.

Alternatively or additionally, one or more thresholds for a change of $Z(f_n)_{ratio}$ may be determined for the whole frequency range or at least part of the frequency range for determining wound healing. When the change of $Z(f_n)_{ratio}$ meets a determined threshold, a level of wound healing corresponding to the threshold may be determined.

Example thresholds for $Z(f_n)_{ratio}$ may comprise percentages, e.g. 130%, 160% and 180%, for example in FIG. 3. Thresholds for the change of the $Z(f_n)_{ratio}$ may be defined for different values of the derivative of $Z(f_n)_{ratio}$ on a logarithmic frequency scale.

The wound healing may be determined based on the change of the $Z(f_n)_{ratio}$ over time, $Z(f_n)_{ratio}$ at a high end 304 of the frequency range, $Z(f_n)_{ratio}$ at a low end 304 of the frequency range and/or decreasing difference between $Z(f_n)$ $_{ratio}$ at a high end 304 and low end 306 the frequency range. Accordingly, the $Z(f_n)_{ratio}$ changes as the wound heals, whereby the frequency response evens out over the frequency range.

The wound healing may be determined on the basis of $Z(f_n)_{ratio}$ decreasing over time at the high end 304 of the frequency range in the illustrated frequency range in FIG. 3. At the high end of the frequency range the measured impedance is significantly affected by the capability of the cellular membranes to conduct electricity. The capability of the cellular membranes to conduct electricity is negatively affected by missing and/or damaged cellular membranes in the wound, whereby at the beginning of the healing, the wound impedance $Z(f)_w$ is high. When the healing of the wound progresses, cells are generated and cellular membranes are reconstructed, whereby the capability of the wound to conduct electricity is improved and the wound impedance is decreased. The healing of the wound may be observed from the frequency response at the high end of the frequency range, where the impedance of the wound is first higher than the reference impedance and the frequency response decreases from the first day to the ninth day as the healing proceeds. At the high end of the frequencies the capability of the cellular membranes to conduct electricity is better than the bulk extracellular fluid and the current will travel via the cellular membranes and through the extracellular fluid between the cells. One or more thresholds may be determined for the $Z(f_n)_{ratio}$ for determining corresponding levels of wound healing from the $Z(f_n)_{ratio}$ meeting a specific threshold.

In the low end 306 of the frequencies the wound healing may be determined on the basis of $Z(f_n)_{ratio}$ increasing over time. At the low end of the frequencies the impedance of the wound is first lower than the reference impedance and the frequency response increases from the first day to the ninth day as the healing proceeds and the swelling diminishes. Accordingly, the frequency response at the low end of the frequencies may particularly indicate an amount of extracellular fluid for example in lymphedema.

In the intermediate frequencies 308 a change of the frequency response $Z(f_n)_{ratio}$ decreases from the first day to the ninth day as the healing proceeds and the swelling diminishes. In the intermediate frequencies, a level of the healing of the wound may be determined on the basis of a change of the correspondence between the wound impedance and the reference impedance. The change may be determined on the basis of a derivative of the $Z(f_n)_{ratio}$. A value of the change at a specific frequency may be obtained on the basis of the slope of the $Z(f_n)_{ratio}$ at the specific frequency for determining a level of the wound healing. Accordingly, the level of the healing of the wound may be determined on the basis of the slope of the $Z(f_n)_{ratio}$. The wound may be determined to be healed, when the slope is sufficiently small.

In an embodiment there is provided an arrangement comprising means for measuring a wound impedance by a first tetrapolar arrangement of electrodes arranged on both sides of a wound, means for measuring a reference impedance by a second tetrapolar arrangement of electrodes arranged on one side of the wound, means for determining wound healing on the basis of the wound impedance and the reference impedance measured over a frequency range.

It should be appreciated that various embodiments described herein may be implemented by means that are caused to perform one or more functions described in the embodiments. Suitable means may comprise means known to the skilled person, for example a controller, a computer, a processor, a memory device, a computer program and/or a virtual machine that may be combined in various ways to cause one or more functions described in the embodiments. For example, a computer program may be stored on a memory device accessible to computer, a processor and/or a virtual machine for execution of the code.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

The present invention can be used for determining wound healing for example in situation where the wound has penetrated the superficial parts of the skin, such as surgical wounds. The present invention can also be used for determining wound healing of internal wounds such as encapsulated wounds or internal traumas. Thus, the invention finds application in post-operative monitoring of wound-healing. The invention can also be used for evaluating timely healing of wounds which are difficult or impossible to assess visually, for example wounds which are covered by orthopaedic casts. Naturally, the present invention can also be used for monitoring wound healing where only superficial layers of the tissue has a healing wound.

REFERENCE SIGNS LIST

102 Wound
103, 105 End of the wound
104, 106 One side of the wound
108 Controller
A, B, C, D, E, F, G Electrode
H, I, J, K, L Electrode
202, 204, 206 Phase of the method in FIG. 2
302 Frequency response
306 Low end of frequency
304 High end of frequency
308 Intermediate frequency
311, 313, 319 Post-operative day

CITATION LIST

Non-Patent Literature

Kekonen A, Bergelin M, Eriksson J-E, Vaalasti A, Ylänen H, Viik J (2017) Bioimpedance measurement based evaluation of wound healing. Physiol Meas DOI:10.1088/1361-6579/aa63d6.

The invention claimed is:

1. A method for measuring wound healing, comprising:
measuring a wound transfer impedance by a first tetrapolar arrangement of electrodes arranged on both sides of a wound; wherein the first tetrapolar arrangement of electrodes comprises two current feeding electrodes and two voltage sensing electrodes, wherein the measuring of the wound transfer impedance comprises:
   applying, by the two current feeding electrodes, an excitation signal, and
   measuring, by the voltage sensing electrodes, an impedance based on a voltage difference induced by the excitation signal,
measuring a reference transfer impedance by a second tetrapolar arrangement of electrodes arranged on one side of the wound; wherein the second tetrapolar arrangement of electrodes comprises two current feeding electrodes and two voltage sensing electrodes, wherein the measuring of the reference transfer impedance comprises:
   applying, by the two current feeding electrodes, an excitation signal, and
   measuring, by the voltage sensing electrodes, an impedance based on a voltage difference induced by the excitation signal,
wherein the wound transfer impedance and the reference transfer impedance are measured over a frequency range, and
determining, by a controller, at least one level of the wound healing on the basis of a ratio between the wound transfer impedance and the reference transfer impedance and a change of said ratio over at least part of the frequency range,
wherein the change of said ratio meets a predefined threshold.

2. The method according to claim 1, wherein the wound transfer impedance and the reference transfer impedance are measured in a time-division manner by at least partly shared electrodes.

3. The method according to claim 1, wherein at least one level of the wound healing is determined based on the change of the ratio over time, a ratio of the wound transfer impedance and the reference transfer impedance at a high end of the frequency range, a ratio of the wound transfer impedance and the reference transfer impedance at a low end of the frequency range and/or decreasing difference between ratios of the wound transfer impedance and the reference transfer impedance at a high end and low end of the frequency range.

4. The method according to claim 1, wherein the frequency range comprises frequencies less than frequencies where current flow caused by the first or second tetrapolar arrangements passes through cellular membrane of human or animal skin and/or fascia under the human or animal skin.

5. The method according to claim 1, wherein the frequency range comprises frequencies where the excitation signal of the first and/or or second tetrapolar arrangements cause conduction of the current along cellular membrane surfaces.

6. The method according to claim 1, wherein the first tetrapolar arrangement and/or the second tetrapolar arrangement comprises excitation electrodes and measurement electrodes arranged in a parallel arrangement around the wound or in a sequential arrangement across the wound.

7. An arrangement for measuring wound healing comprising:
a first tetrapolar arrangement of electrodes adapted to be arranged on both sides of a wound for measuring a wound transfer impedance, wherein the first tetrapolar arrangement of electrodes comprises two current feeding electrodes and two voltage sensing electrodes, wherein the measuring of the wound transfer impedance comprises:
   applying, by the two current feeding electrodes, an excitation signal, and
   measuring, by the voltage sensing electrodes, an impedance based on a voltage difference induced by the excitation signal,
a second tetrapolar arrangement of electrodes adapted to be arranged on one side of the wound for measuring a reference transfer impedance, wherein the second tetrapolar arrangement of electrodes comprises two current feeding electrodes and two voltage sensing electrodes, wherein the measuring of the reference transfer impedance comprises:
   applying, by the two current feeding electrodes, an excitation signal, and
   measuring, by the voltage sensing electrodes, an impedance based on a voltage difference induced by the excitation signal,
and a controller configured to determine at least one level of the wound healing on the basis of at least one of:
  a ratio between the wound transfer impedance and the reference transfer impedance; and
  a change of said ratio over at least part of a frequency range, wherein the change of said ratio meets a predetermined threshold,
wherein the wound transfer impedance and the reference transfer impedance are measured over the frequency range.

8. The arrangement according to claim 7, wherein the wound transfer impedance and the reference transfer impedance are measured in a time-division manner by at least partly shared electrodes.

9. The arrangement according to claim 7, wherein at least one level of the wound healing is determined based on the change of the ratio over time, a ratio of the wound transfer impedance and the reference transfer impedance at a high end of the frequency range, a ratio of the wound transfer impedance and the reference transfer impedance at a low end of the frequency range and/or decreasing difference between ratios of the wound transfer impedance and the reference transfer impedance at a high end and low end of the frequency range.

10. The arrangement according to claim 7, wherein the first tetrapolar arrangement and/or the second tetrapolar arrangement comprises excitation electrodes and measurement electrodes arranged in a parallel arrangement around the wound or in a sequential arrangement across the wound.

11. The arrangement according to claim 7, wherein the level of the healing of the wound is determined on the basis of the slope of the ratio between the wound transfer impedance and the reference transfer impedance over the frequency range.

12. The arrangement according to claim 7, wherein the frequency range comprises frequencies between 150 Hz and 40 kHz.

13. The method according to claim 1, wherein the level of the healing of the wound is determined on the basis of the slope of the ratio between the wound transfer impedance and the reference transfer impedance over the frequency range.

14. The method according to claim 1, wherein the frequency range comprises frequencies between 150 Hz and 40 kHz.

15. A processor and memory device, the memory device configured to store a computer program to cause a method for measuring wound healing to be performed, the method comprising:
  measuring a wound transfer impedance by a first tetrapolar arrangement of electrodes arranged on both sides of a wound; wherein the first tetrapolar arrangement of electrodes comprises two current feeding electrodes and two voltage sensing electrodes, wherein the measuring of the wound transfer impedance comprises:
    applying, by the two current feeding electrodes, an excitation signal, and
    measuring, by the voltage sensing electrodes, an impedance based on a voltage difference induced by the excitation signal,
  measuring a reference transfer impedance by a second tetrapolar arrangement of electrodes arranged on one side of the wound; wherein the second tetrapolar arrangement of electrodes comprises two current feeding electrodes and two voltage sensing electrodes, wherein the measuring of the reference transfer impedance comprises:
    applying, by the two current feeding electrodes, an excitation signal, and
    measuring, by the voltage sensing electrodes, an impedance based on a voltage difference induced by the excitation signal,
  wherein the wound transfer impedance and the reference transfer impedance are measured over a frequency range, and
  determining, by a controller, at least one level of the wound healing on the basis of a ratio between the wound transfer impedance and the reference transfer impedance and a change of said ratio over at least part of the frequency range,
wherein the change of said ratio meets a predefined threshold.

* * * * *